(12) United States Patent
Martin

(10) Patent No.: US 9,181,323 B2
(45) Date of Patent: Nov. 10, 2015

(54) METHOD FOR PREPARING A CONCENTRATE OF FACTOR XI

(75) Inventor: Jean-François Martin, Lille (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 0 days.

(21) Appl. No.: 14/112,175

(22) PCT Filed: Apr. 19, 2012

(86) PCT No.: PCT/EP2012/057227
§ 371 (c)(1),
(2), (4) Date: Oct. 16, 2013

(87) PCT Pub. No.: WO2012/143483
PCT Pub. Date: Oct. 26, 2012

(65) Prior Publication Data
US 2014/0046028 A1    Feb. 13, 2014

(30) Foreign Application Priority Data

Apr. 20, 2011 (FR) ...................... 11 53437

(51) Int. Cl.
*C07K 14/745* (2006.01)
*C12N 9/64* (2006.01)

(52) U.S. Cl.
CPC ............ *C07K 14/745* (2013.01); *C12N 9/6443* (2013.01); *C12Y 304/21027* (2013.01)

(58) Field of Classification Search
None
See application file for complete search history.

(56) References Cited

U.S. PATENT DOCUMENTS 5,252,217 A * 10/1993 Burnouf-Radosevich et al. .............................. 210/635

FOREIGN PATENT DOCUMENTS

EP    0 512 883 A1    11/1992
EP    0798003 B1 *    5/2006

OTHER PUBLICATIONS

ZetaPLUS product information from Cuno—Retrieved from < http://www.sefiltra.com/pdf/Zeta_Plus_Biocap_09.pdf > and < http://multimedia.3m.com/mws/mediawebserver?mwsId=SSSSSufSevTsZxtUNx2UnY_eevUqevTSevTSevTSeSSSSSS--&fn=DOC00645%20-%20LITZPSC1.E.pdf > on Aug. 18, 2014.*
Aledort et al., "United States' Factor XI-Deficiency Patients Need a Safer Treatment", American Journal of Hematology 80:301-302 (2005).*
Chtourou, S. & Poulle, M. (2012). Factor XI. In J. Bertolini, N. Goss & J. Curling (Ed.), In Production of Plasma Proteins for Therapeutic Use (Chapt. 7, pp. 93-100). New York:Wiley. p. 96 provided.*
Burnouf-Radosevich et al., "A therapeutic, highly purified factor XI concentrate from human plasma," Transfusion, vol. 32, No. 9, pp. 861-867, 1992.
International Search Report issued in application No. PCT/EP2012/057227 on Jul. 4, 2012.

* cited by examiner

Primary Examiner — Suzanne M Noakes
(74) Attorney, Agent, or Firm — Foley & Lardner LLP

(57) ABSTRACT

The invention concerns a concentrate of human Factor XI having high specific activity prepared using a method comprising a filtration-adsorption step and a chromatography step on cation exchange resin. The concentrate obtained is fully adapted for therapeutic use as substitution therapy in cases of Factor XI deficiency.

17 Claims, No Drawings

METHOD FOR PREPARING A CONCENTRATE OF FACTOR XI

FIELD OF THE INVENTION

The present invention concerns a method for preparing Factor XI from a cryosupernatant of plasma precipitate, comprising an adsorption-filtration step and a chromatography step on cation exchange resin.

STATE OF THE ART

Factor XI or the precursor of plasma thromboplastin is a glycoprotein which is part of the contact pathway in the mechanism of haemostasis, through its activating action on Factor IX, and is part of the fibrinolysis pathway through its activating action on plasminogen.

Factor XI deficiency is hereditary and is transmitted as a recessive autosomal character. It is a rare deficiency but widespread in some populations of Middle-East origin.

As is the case for other factors whose deficiency is rare (Factor V, Factor XIII, Factor X), therapeutic products purified from human plasma are still scarce or inexistent and the sole substitution therapy uses total plasma or the supernatant fraction of plasma cryoprecipitate, but this entails the simultaneous injection of useless quantities of other plasma proteins and hence a risk of various major secondary reactions after multiple injections.

Patent EP 512 883 B1 describes a method for preparing a concentrate of Factor XI comprising a filtration-adsorption step and a chromatography step on cation exchange resin. The filtration-adsorption step of the method described in this patent is performed on a series of depth filters composed of cellulose and perlites carrying negative charges and a small quantity of positively charged resin. These filters have a porosity ranging from 0.5 to 2 μm and have the property of binding FXI. The yield of FXI purification at this step is about 50% and the specific activity of the eluted FXI is about 10-20 U/mg. However, in the event of a reduced yield, the subsequent chromatography step can be strongly influenced and hence cause non-conformity of the end product for faulty FXI concentration.

There is therefore a true need to develop a method for purifying FXI allowing the yields of the purification method to be increased, in particular after the adsorption-filtration step, so that it is possible to avoid any problem of non-conformity of the end product.

SUMMARY OF THE INVENTION

The present invention therefore concerns a method for preparing a concentrate of Factor XI, comprising a filtration-adsorption step conducted on a filter composed of cellulose and perlites and a small quantity of positively charged resin, the said filter having a grade ranging from 0.1 to 0.4 μm, preferably from 0.2 to 0.4 μm, preferably from 0.25 to 0.35 μm, and preferably 0.3 μm; and a chromatography step on cation exchange resin.

At the adsorption-filtration step of the preparation method of the present invention, the elution of FXI adsorbed on the filter is performed using a solution adjusted to a pH of 5.5 to 6.5, for example comprising sodium citrate, disodium phosphate, potassium phosphate, disodium EDTA and sodium chloride, the concentration of said sodium chloride being higher than 0.5 M, preferably higher than or equal to 0.6 M or preferably higher than or equal to 0.75 M or preferably equal to 1 M.

The adsorption-filtration step may also comprise washing of the filter prior to elution of the adsorbed FXI, using a buffer adjusted to a pH of 5.5 to 6.5 for example comprising sodium citrate, disodium phosphate, potassium phosphate and sodium chloride, the concentration of said sodium chloride being equal to or lower than 0.5 M, preferably equal to or lower than 0.4 M, preferably equal to 0.3 M.

Preferably the filtering flow rate of the adsorption-filtration step lies in the range of 7 to 20 mL/h/cm$^2$, preferably 10 to 15 mL/h/cm$^2$, preferably 12 to 14 m L/h/cm$^2$.

Preferably the volume load used at the adsorption-filtration step lies in the range of 11 to 50 mL/cm$^2$, preferably 20 to 40 mL/cm$^2$, preferably 25 to 35 mL/cm$^2$.

The Factor XI fraction resulting from the adsorption-filtration step undergoes a diafiltration step before the purification step by chromatography. The method of the invention may also comprise additional steps of concentration and viral inactivation between the adsorption-filtration step and the purification step by chromatography.

During the chromatography step, the cation exchange resin is preferably equilibrated with a buffer adjusted to a pH of 5.5 to 6.5 comprising sodium citrate, sodium chloride, lysine and arginine. The cation exchange resin is then loaded with the FXI resulting from the adsorption-filtration step, and washed with a buffer adjusted to a pH of 6.1 to 6.9 comprising sodium citrate, disodium phosphate, potassium phosphate, sodium chloride, lysine and arginine. The Factor XI is finally eluted from the cation exchange resin with a buffer adjusted to a pH of 7 to 8 comprising sodium citrate, disodium phosphate, potassium phosphate, sodium chloride, lysine and arginine in which the concentration of sodium chloride is between 0.15 and 0.20 M.

The resulting solution of FXI is preferably stabilised through the addition of antithrombin III, heparin and C1-inhibitor and may at this stage be subjected to a viral removal step preferably by filtering through a grade 15 nm filter. The FXI solution is then packaged and lyophilised. The stabilised FXI solution is in particular packaged as a pharmaceutical product.

The present invention also concerns a composition of FXI able to be obtained using the method of the invention.

The applicant has surprisingly discovered that the use of a filter composed of cellulose and perlites, comprising a charged resin and having a lower grade than the filters used in the state of the art and in particular in the method of patent EP 512 883 not only allows adsorbing of the FXI to a greater extent and hence the obtaining of a significant increase in FXI yield and in FXI purity, but also allows a significant increase in volume load, the filtering flow rate used at this step, compared with the method described in patent EP 512 883. This filter therefore offers greater industrial advantages than the filters used in the method of patent EP 512 883 such as a reduction in the number of filter cartridges and hence a reduction in occupied space in production facilities, upgrading to large-scale, simplified installation and assembly, and a reduction in the overall time of the fabrication process. Quite unexpectedly the method of the present invention, which uses filters having a grade ranging from 0.1 to 0.4 μm, preferably 0.2 to 0.4 μm, preferably 0.25 to 0.35 μm and preferably of 0.3 μm facilitates the adsorbing of FXI at the adsorption-filtration step even when the protein load and flow rate used are significantly increased.

It therefore appears that the novel method of the invention allows both an improvement in the yield and specific activity of the FXI purified at the adsorption-filtration step whilst reducing the duration of this step. This leads to a reduction in costs and in the production time of FXI.

DETAILED DESCRIPTION OF EMBODIMENTS

The present invention concerns a method for preparing a concentrate of Factor XI comprising a filtration-adsorption step, selectively retaining Factor XI, and a chromatography step on cation exchange resin.

The first step of the purification method corresponds to a filtration-adsorption step performed on a depth filter. The filter used is composed of cellulose and perlites, and comprises a charged resin. The filter used is of a grade ranging from 0.2 to 0.4 µm, preferably 0.2 to 0.4 µm, preferably 0.25 to 0.35 µm, and further preferably 0.3 µm. In one preferred embodiment, the filter used is a Sartoclear® S5P filter (marketed by Sartorius stedim biotech GmbH) and having a grade of 0.3 µm. Other comparable filters that are commercially available may also be used.

In one particular embodiment, the method of the invention is implemented from a supernatant of plasma cryoprecipitate. The supernatant used in the present invention can be obtained from any suitable source and preferably corresponds to plasma of human origin.

In one preferred embodiment, the purification method of the present invention applies to the supernatant of human plasma cryoprecipitate and can be adapted to volumes of at least 1000 liters to 1200 liters. It also advantageously allows the production of Factor XI for therapeutic use from about 1100 liters of plasma and within a fairly short time (about 28 hours) including an optional viral inactivation treatment time (about 8 hours).

In one preferred embodiment, the method of the invention comprises an adsorption step of FXI on the depth filter by passing the supernatant of plasma cryoprecipitate through the filter. The filter is then advantageously washed with a buffer adjusted to a pH of 5 to 7, preferably pH 6, comprising sodium citrate, disodium phosphate, potassium phosphate and sodium chloride. The concentration of sodium chloride in said buffer is preferably equal to or less than 0.3 M and is preferably 0.06 M. This filtering step removes most plasma proteins.

In one preferred embodiment, the filter is then washed with a buffer adjusted to a pH of 5 to 7 and preferably pH 6, comprising sodium citrate, disodium phosphate, potassium phosphate and sodium chloride. The concentration of sodium chloride in said buffer is preferably equal to or less than 0.5 M, preferably equal to or less than 0.4 M, and preferably it is 0.3 M. This washing step removes the plasma proteins weakly adsorbed on the filter and increases the purity of the FXI eluted at the following step.

In one preferred embodiment, the Factor XI which remained adsorbed on the filter is then desorbed or eluted by increasing the ionic strength of the wash buffer. The Factor XI is therefore desorbed using a buffer whose final concentration of sodium chloride is higher than 0.5 M, preferably higher than or equal to 0.6 M, preferably higher than or equal to 0.75 M, further preferably it is 1 M. In one preferred embodiment the elution buffer may also comprise a small quantity of protease inhibitors, advantageously antithrombin III (AT III) to protect the Factor XI against the action of any proteases and hence its activation. Heparin and/or C1-inhibitor may advantageously be added to stabilise the mixture obtained.

In one preferred embodiment of the present invention, the adsorption-filtration step of FXI is conducted at a filtering flow rate ranging from 7 to 20 mL/h/cm$^2$, preferably 10 to 15 mL/h/cm$^2$, preferably 12 to 14 mL/h/cm$^2$. In the context of the present invention, by « filtering flow rate» is meant the linear flow rate calculated by measuring the volume or weight filtered per unit of time and per unit surface area. This flow rate is maintained for every step of the adsorption/filtration step.

In one preferred embodiment of the present invention, the adsorption-filtration step of FXI is conducted with a volume load ranging from 11 to 50 mL/cm$^2$ preferably 20 to 40 mL/cm$^2$, preferably 25 to 35 mL/cm$^2$. In the context of the present invention by « volume load» is meant the volume or weight of solution (for example of precipitation cryosupernatant) that is passed per unit of filtering surface.

In one preferred embodiment, the FXI solution obtained after the adsorption-filtration step is subjected to viral inactivation treatment. This viral inactivation treatment is preferably performed using the solvent and/or detergent method of treatment known to persons skilled in the art. In one preferred embodiment of the invention, the viral inactivation treatment is conducted in the presence of Tween 80, preferably at a final concentration of 1% (w/v) and Tri-n-Butyl Phosphate or TnBP, preferably at a final concentration of 0.3% (v/v). The viral inactivation treatment is preferably conducted for a time of at least 8 hours.

In one preferred embodiment, the FXI solution obtained after the adsorption-filtration step is dialysed and can be concentrated and frozen to −80° C. for storage before carrying out a possible viral inactivation step.

The FXI solution is then purified by chromatography on cation exchange resin. This chromatography step additionally allows the complete removal of the residual products remaining after the viral inactivation step, if this step is carried out. This chromatography step notably allows the removal of subsisting contaminating proteins.

The fraction containing the FXI desorbed from the filter, dialysed and optionally concentrated, optionally frozen and virally inactivated, is injected into a chromatography column comprising a cation exchange resin. In one preferred embodiment, the cation exchange resin is more particularly Sulfate-Sepharose Fast Flow (S-Sepharose FF). S-Sepharose gel unexpectedly has a very high retaining capacity of Factor XI (from 300 to 450 U/ml of gel) for example making it possible to avoid a subsequent concentration step of FXI via an ultrafiltration step which would lead to loss of yield. In addition, binding to S-Sepharose FF allows the FXI to be eluted with a buffer having properties comparable to those of a physiological buffer whereas other resins e.g. containing sulfylpropyl groups require more drastic eluting conditions involving the setting up of a diafiltration step to return to conditions of an injectable product.

In one preferred embodiment, the cation exchange resin is equilibrated with a buffer adjusted to a pH of 5.5 to 6.5, preferably pH 6, composed of sodium citrate, sodium chloride, lysine and arginine.

In one preferred embodiment, the cation exchange resin is loaded with the solution containing the FXI derived from the adsorption-filtration step which is dialysed and optionally concentrated and virally inactivated. Washing is then preferably performed with the equilibrating buffer of pH 5.5 to 6.5 preferably pH 6, composed of sodium citrate, sodium chloride, lysine and arginine. A second washing is then preferably performed with a buffer adjusted to a pH of between 6.1 and 6.9, preferably pH 6.5, comprising sodium citrate, disodium phosphate, potassium phosphate, sodium chloride, lysine and arginine.

The Factor XI is then eluted from the cation exchange resin using a buffer comparable to the above-mentioned wash buffer but having a pH of between 7 and 8, preferably pH 7.5 and whose sodium chloride concentration is between 0.15 and 0.20 M, preferably 0.17 M.

In one preferred embodiment, the Factor XI is stabilised after its elution from the cation exchange resin, through the addition of small amounts of protease inhibitors e.g. Antithrombin III, heparin and C1-inhibitor. The Factor XI solution is stabilised with the addition of 0.5 to 3 IU, preferably 1 to 3 IU, preferably 2 to 3 IU of Antithrombin III, 0.5 to 4 IU, preferably 1 to 4 IU, preferably 2 to 4 IU of heparin and 0.5 to 2 IU, preferably 1 to 2 IU, preferably 1.5 to 2 IU of C1-inhibitor per 100 IU of Factor XI.

The resulting stabilised FXI solution may optionally undergo a viral removal step preferably via filtration on a 15 nm grade filter and/or is then sterilised e.g. by filtration, packaged and lyophilised.

In one preferred embodiment, the stabilised and optionally virally filtered solution of Factor XI is packaged as a pharmaceutical product. This packaging may in particular be performed by adding pharmaceutically acceptable excipients.

A further subject of the invention comprises a composition of Factor XI able to be obtained using the method of the invention.

Advantageously the purification factor of the present method is at least 10000 relative to the starting plasma.

The Factor XI obtained with the method of the present invention has specific activity ranging from 80 to 120 U/mg, preferably at least equal to 100 U/mg of proteins.

The high purity of the Factor XI obtained is evidenced by polyacrylamide gel electrophoresis under denaturing conditions (in the presence of SDS) and biochemical analyses, and its innocuousness is evidenced by biological tests on animals.

The concentrate of Factor XI obtained with the method of the present invention is therefore particularly well adapted to therapeutic use, in particular as substitution therapy in cases of congenital or acquired deficiency of Factor XI.

The present invention is illustrated by the examples and embodiments described and illustrated, but it is no way limited thereto insofar as it may have numerous variants accessible to persons skilled in the art.

Example 1

Composition of Factor XI

Starting Material:

Each batch of Factor XI was prepared from a volume of about 1000 liters of supernatant of human plasma cryoprecipitate. The cryoprecipitation supernatant was first clarified on a 1 µm grade filter such as the Profile® II (Pall) filter.

First Purification Step

The cryoprecipitate supernatant was passed through a Sartoclear® S5P (Sartorius) filter of grade 0.3 µm at a flow rate of 13 mL/h/cm$^2$ (i.e. about 14.3 L/h). The volume load used corresponded to 30 mL of cryoprecipitate supernatant/cm$^2$ of filtering surface area, and all filtering was conducted at a temperature of 2 to 8° C.

After removing the filtrate containing most of the proteins of the cryoprecipitate supernatant, the filter was washed with buffer comprising 5 mM sodium citrate, 5 mM disodium phosphate, 5 mM potassium phosphate, 0.065 M sodium chloride and adjusted to pH 6 with citric acid At this filtering stage the FXI is adsorbed on the filter.

A more stringent wash step was performed with a buffer comparable to the wash buffer but containing 0.3 M NaCl.

The Factor XI was eluted from the filter by increasing the ionic strength of the wash buffer. The eluting buffer used, to which disodium EDTA was added, also contained 1 M NaCl. To the resulting FXI solution, 0.2 U/ml antithrombin III were added to protect the Factor XI against the action of residual plasma proteases. The disodium EDTA in the buffer also takes part in this protective action.

The FXI solution thus recovered was concentrated about 30 times and dialysed to remove the EDTA using a Pall ultrafiltration system having a cut-off threshold at 10 kD. The expressed flow rate is a linear flow rate. It can be calculated by measuring the volume or weight filtered per unit of time and per unit surface area. This flow rate was maintained for all the steps of the adsorption/filtration step. The dialysis step also allows the FXI fraction to be placed under the osmolality and chemical composition conditions of the equilibrating buffer in the S-Sepharose FF column, to guarantee FXI binding in the column.

The dialysis buffer was composed of 5 mM sodium citrate, 140 mM sodium chloride, 5.5 mM L-lysine and 20 mM arginine, and adjusted to pH 6.

The dialysed solution was passed through a KA2NLP 0.45 µm filter (Pall)+0.22 µm KA2NFP1 (Pall) filter to clarify the solution and optionally remove any bacterial contaminants present.

Viral Inactivation Treatment

The solution containing Factor XI was subjected to treatment with a solvent-detergent known for its efficacy against lipid enveloped viruses (Horowitz et al 1985, Transfusion 25, 516-522) and which comprised 8-hour incubation at 25° C. in the presence of 0.3% tri-n-butyl-phosphate (TnBP) and 1% Tween 80.

Second Purification Step

The objective of this step was to increase the purity of Factor XI (essentially by removing Factor II, Factor VII, Factor X, high molecular weight kininogens, the Prekallikrein Activator, M immunoglobulins, G immunoglobulins, fibronectin and fibrinogen, whilst removing from the solution the solvent-detergent used for viral inactivation treatment.

A chromatography column was used containing a cation exchange resin, more particularly Sulfate-Sepharose Fast Flow gel (S Sepharose FF, manufactured and distributed by Pharmacia, Uppsala, Sweden).

The column was equilibrated with the above-described dialysis buffer.

After loading the protein solution in the column, the column was rinsed with at least 20 volumes of the above-described dialysis buffer pH 6.0 to remove the proteins non-adsorbed on the gel and the viral inactivation agents. The gel was then washed with a buffer solution comprising 10 mM sodium citrate, 5 mM disodium phosphate, 5 mM potassium phosphate, 92 mM sodium chloride, 27 mM lysine and 11.5 mM arginine, pH 6.5, to elute the proteins weakly adsorbed on the gel.

The Factor XI was eluted from the column by increasing the pH of the buffer to 7.5 and increasing the NaCl concentration to 170 mM.

The linear flow rate to pass the equilibrating buffer, wash and eluting solutions was 50 cm/h.

To the eluted FXI solution there were added three stabilisers:

Antithrombin III in an amount of about 3 IU Antithrombin per 100 IU of FXI;

C1-inhibitor in an amount of about 2 U of C1-inhibitor per 100 IU of FXI; and heparin in an amount of about 4 IU heparin per 100 IU of FXI.

The stabilised solution was filtered through 0.22 µm Millipak 20, dispensed (10 ml per bottle) and lyophilised. It may be filtered through a grade 15 nm filter before 0.22 µm filtering and dispensing into bottles.

Biochemical and Biological Analyses of the Factor XI Concentrate

The purity yields (%) of FXI (IU/mg) and «activation levels» measured using the ratio of activated Factor XI/Factor XI (FXIa/FXI) obtained at the different unit steps of the method are illustrated in Table 1 below:

TABLE 1

| Steps | Mean of 3 batches |
|---|---|
| Cryosupernatant | |
| FXI (IU/mL) | 0.74 |
| FXI (Total IU) | 23660 (100%) |
| Specific activity (IU/mg) | 0.01 |
| FXIa/FXI (µg/IU) | 0.236 |
| Sartoclear eluate | |
| FXI (IU/mL) | 4.1 |
| FXI (Total IU) | 17763 (82%) |
| Specific activity (IU/mg) | 31.3 |
| FXIa/FXI (µg/IU) | 3.1 |
| After Ultrafiltration | |
| FXI (IU/mL) | 85.1 |
| FXI (Total IU) | 15630 (74%) |
| Specific activity (IU/mg) | 23.3 |
| FXIa/FXI (µg/IU) | ND |
| S-Sepharose eluate | |
| FXI (IU/mL) | 121 |
| FXI (Total IU) | 12126 (55%) |
| Specific activity (IU/mg) | 292 |
| FXIa/FXI (µg/U) | 0.46 |
| Stabilised | |
| FXI (IU/mL) | 102.7 |
| Specific activity (IU/mg) | 95.7 |
| FXIa/FXI (µg/U) | <0.001 |

With the method of the invention, it is possible to obtain a filtration/adsorption yield of FXI of about 80% and FXI purity of about 20 to 40 IU/mg. By way of comparison, the method described in patent EP 512 883 allows a filtration/adsorption yield to be obtained of about 50% and FXI purity of about 10 to 20 IU/mg.

The yield and purity obtained in the present invention therefore prove to be significantly higher than obtained when implementing the method of the prior art. In addition, the method of the invention was performed under FXI binding and eluting conditions in which the protein load and filter flow rate were respectively increased by a factor of 3 and a factor of 2 compared with the conditions applied in the method of patent EP 512 883.

As a result, the method of the invention allows a significant reduction in the cost and production time of FXI, whilst providing a Factor XI having a purity level higher than that described in the state of the art for the filtration/adsorption step.

The removal of the proteins present in the cryoprecipitate supernatant during the purification method is illustrated in following Table 2. The results were compared with the data reported for the method in patent EP 512 883.

Removal of Proteins During FXI Purification

| Depth filter eluate of the invention | | |
|---|---|---|
| | FXI solution obtained with the method of the invention (mean of 3 batches) | FXI solution obtained with the method of EP 0 512 883 (mean of 3 batches) |
| Proteins (g/L) | 3.8 | 8.2 |
| High molecular weight kininogens (µg/mL) | ≥300 | 418 |
| Factor II (IU/mL) | 1.04 | 8.8 |
| G Immunoglobulins (mg/mL) | 0.28 | 0.9 |
| M Immunoglobulins (mg/mL) | 0.21 | 0.26 |
| Fibronectin (mg/mL) | 0.018 | 0.09 |
| C3 component of complement (mg/mL) | 0.041 | 0.1 |
| C1-Inhibitor (mg/mL) | 0.011 | 0.029 |
| α-2 Macroglobulin (mg/mL) | 0.039 | 0.17 |
| S-Sepharose FF eluate | | |
| Proteins (g/L) | 0.42 | 0.64 |
| High molecular weight kininogens (µg/mL) | <10 | 123 |
| Factor II (IU/mL) | <0.1 | <0.126 |
| G Immunoglobulins (mg/mL) | 0.003 | 0.02 |
| M Immunoglobulins (mg/mL) | 0.011 | 0.022 |
| Fibronectin (mg/mL) | <0.003 | 0.03 |
| C3 component of complement (mg/mL) | <0.008 | <0.03 |
| C1-Inhibitor (mg/mL) | 0.01 | 0.044 |
| α-2 Macroglobulin (mg/mL) | <0.003 | <0.01 |
| Stabilised S-Sepharose FF eluate | | |
| Proteins (g/L) | 1.1 | 0.73 |
| High molecular weight kininogens (µg/mL) | <10 | 49 |
| Factor II (IU/mL) | <0.1 | <0.126 |
| G Immunoglobulins (mg/mL) | 0.004 | 0.018 |
| M Immunoglobulins (mg/mL) | 0.01 | 0.01 |
| Fibronectin (mg/mL) | <0.004 | 0.01 |
| C3 component of complement (mg/mL) | <0.008 | <0.03 |
| C1-Inhibitor (mg/mL) | 0.52* | 0.53* |
| α-2 Macroglobulin (mg/mL) | <0.003 | <0.01 |

*after addition for stabilisation

The absence of residual contamination by coagulation factors and constituents of the kinin system (kininogens) was carefully controlled using conventional methods.

After reconstituting the lyophilised product, conventional tolerance tests on animals were performed:
thrombogenicity test in rabbits;
hypotension test in rats;
toxicity test in mice.

The tests on rabbits showed that the composition of the invention is not thrombogenic since ED50 (effective dose for 50%) is higher than 1000 U FXI/kg whereas this same value is 40 to 60 U/kg for a concentrate of PPSB (coagulating fraction composed of proconvertin, prothrombin, Stuart factor, anti-haemophilic factor 13) which is therefore much more thrombogenic and may effectively lead to phenomena of thrombosis and disseminated intravascular coagulation in man at a high dose.

The FXI composition of the invention does not cause phenomena of hypotension when injected via intravenous route into rats at a dose of 50 U FXI/kg. This animal model is highly sensitive to the presence of plasma components having vasoactive properties and showed the absence of these components in the Factor XI composition obtained using the described method.

When injected via intravenous route into mice at high dose (2500 U/kg) it does not cause any lethality or disturbed behaviour over a 7-day period.

The invention claimed is:

1. A method for preparing a concentrate of Factor XI (FXI), comprising
    a) filtration-adsorption of a supernatant of human plasma cryoprecipitate using a filter comprising cellulose and perlites and a charged resin, wherein the filter has a grade ranging from 0.1 to 0.4 µm, wherein the filtration-adsorption step comprises passing the supernatant of plasma cryoprecipitate through the filter to adsorb FXI on the filter, and desorbing or eluting the adsorbed FXI; and
    b) chromatography of the product of step a) on a cation exchange resin to obtain a solution of Factor XI.

2. The method according to claim 1, wherein the filter has a grade ranging from 0.2 to 0.4 µm.

3. The method according to claim 2, wherein the filter has a grade ranging from 0.25 to 0.35 µm.

4. The method according to claim 3, wherein the filter has a grade of 0.3 µm.

5. The method according to claim 1, wherein the FXI adsorbed on the filter is desorbed or eluted using a solution adjusted to a pH of 5.5 to 6.5 comprising sodium citrate, disodium phosphate, potassium phosphate, disodium EDTA and sodium chloride, the concentration of said sodium chloride being higher than 0.5 M.

6. The method according to claim 5, wherein the concentration of said sodium chloride in said solution is higher than or equal to 0.6 M.

7. The method according to claim 6, wherein the concentration of said sodium chloride in said solution is higher than or equal to 0.75 M.

8. The method according to claim 7, wherein the concentration of said sodium chloride in said solution is 1 M.

9. The method according to claim 1, wherein step a) further comprises washing the filter prior to eluting the adsorbed FXI, using a buffer adjusted to a pH of 5.5 to 6.5 comprising sodium citrate, disodium phosphate, potassium phosphate and sodium chloride, the concentration of said sodium chloride being equal to or lower than 0.5 M.

10. The method according to claim 9, wherein the concentration of said sodium chloride in said buffer is equal to or lower than 0.4 M.

11. The method according to claim 10, wherein the concentration of said sodium chloride in said buffer is 0.3 M.

12. The method according to claim 1, further comprising an additional step for viral inactivation between step a) and step b), and/or a virus removal step after step b).

13. The method according to claim 1, wherein the cation exchange resin of step b) is equilibrated with a buffer adjusted to a pH of 5.5 to 6.5 comprising sodium citrate, sodium chloride, lysine and arginine.

14. The method according to claim 1, wherein the cation exchange resin of step b) is loaded with the FXI resulting from step a), then washed with a buffer adjusted to a pH of 6.1 to 6.9 comprising sodium citrate, disodium phosphate, potassium phosphate, sodium chloride, lysine and arginine.

15. The method according to claim 1, wherein the solution of Factor XI obtained at step b) is stabilised through the addition of 0.5 to 3 IU Antithrombin III, 0.5 to 4 IU of heparin and 0.5 to 2 IU of C1-inhibitor per 100 IU of Factor XI.

16. The method according to claim 1, further comprising packaging the stabilised FXI solution as a pharmaceutical product.

17. The method according to claim 1, further comprising lyophilisation of the Factor XI solution obtained from step b).

* * * * *